(12) United States Patent
Hong

(10) Patent No.: US 12,156,964 B2
(45) Date of Patent: Dec. 3, 2024

(54) ULTRASONIC DEVICE FOR ULTRASOUND ASSISTED LIPOPLASTY

(71) Applicant: LHBioMed Co.,Ltd, Wonju-si (KR)

(72) Inventor: Seong Soo Hong, Yongin-si (KR)

(73) Assignee: LHBioMed Co., Ltd, Wonju-si (KR)

( * ) Notice: Subject to any disclaimer, the term of this patent is extended or adjusted under 35 U.S.C. 154(b) by 162 days.

(21) Appl. No.: 17/984,528

(22) Filed: Nov. 10, 2022

(65) Prior Publication Data

US 2024/0050639 A1    Feb. 15, 2024

(30) Foreign Application Priority Data

Aug. 10, 2022   (KR) .......................... 10-2022-0099724

(51) Int. Cl.
*A61M 1/00*  (2006.01)
*A61N 7/02*  (2006.01)

(52) U.S. Cl.
CPC ................ *A61M 1/89* (2021.05); *A61M 1/76* (2021.05); *A61N 7/02* (2013.01); *A61M 2205/058* (2013.01); *A61N 2007/025* (2013.01)

(58) Field of Classification Search
CPC ........ A61M 1/89; A61M 3/0283; A61M 1/76; A61M 2205/058; A61M 1/77; A61M 1/774
See application file for complete search history.

(56) References Cited

U.S. PATENT DOCUMENTS

2021/0093757 A1 * 4/2021 Turer .................. A61B 5/0537
2022/0211412 A1   7/2022 Hong

FOREIGN PATENT DOCUMENTS

| EP | 3854454 A1 | 7/2021 | |
| KR | 1020170053981 A | 5/2017 | |
| KR | 1020220099167 A | 7/2022 | |
| WO | WO-2021119286 A1 * | 6/2021 | .............. A61M 1/76 |

* cited by examiner

*Primary Examiner* — Gerald Johnson
(74) *Attorney, Agent, or Firm* — Dinsmore & Shohl LLP; Yongsok Choi, Esq.

(57) ABSTRACT

An ultrasonic device for an ultrasound-assisted lipoplasty is provided. The ultrasonic device according to one embodiment of the present disclosure includes: a handpiece; an ultrasonic driving unit provided inside the handpiece; a probe including one end portion connected to the ultrasonic driving unit inside the handpiece and configured to extend outward of the handpiece from the one end portion; and a protection unit formed to extend along a longitudinal direction of the probe and to surround an outer circumferential surface of the probe. A heat-insulation member is provided in at least a portion of an inner circumferential surface of the protection unit.

7 Claims, 2 Drawing Sheets

ULTRASONIC DEVICE FOR ULTRASOUND ASSISTED LIPOPLASTY

CROSS-REFERENCE TO RELATED APPLICATION

This application claims priority to Korean Patent Application No. 10-2022-0099724 filed on Aug. 10, 2022, the entire contents of which are herein incorporated by reference.

TECHNICAL FIELD

The present disclosure relates to an ultrasonic device for ultrasound-assisted lipoplasty, and more particularly, to an ultrasonic device that is inserted into a body, and crushes and emulsifies adipose tissues with ultrasound and suctions the emulsified tissues.

BACKGROUND

Recently, cosmetic surgeries steadily increase with increasing an interest in appearance. Among such cosmetic surgeries, a liposuction accounts for about 14.6% of all entire cosmetic surgeries. As the obesity increases and interest in body shape increases, the demand for liposuction is also increasing. It is known that more than 30,000 cases of liposuction are performed annually in Korea, and the related market is rapidly increasing overseas as well.

Liposuction is a type of cosmetic surgery which suctions and removes an accumulated subcutaneous adipose layer for the purpose of losing weight and body shape correction. As such a liposuction, a suction-assisted lipoplasty (SAL), which is a method of suctioning and removing adipose through a cannula using a negative pressure generated by a vacuum pump, is the most representative. Also, an ultrasound-assisted lipoplasty (UAL) which emulsifies adipose with ultrasound in order to facilitate the suction of adipose is widely used. In addition, there is known a power-assisted lipoplasty (PAL) in which the cannula is moved in the course of suctioning adipose to easily and smoothly perform the suction of adipose.

The ultrasound-assisted lipoplasty is generally performed in such a manner that a probe is inserted into a body to crush and emulsify an adipose tissue by ultrasonic vibration, and then the crushed and emulsified adipose tissue is suctioned through a separate suction process.

When the ultrasound-assisted lipoplasty is performed, heat is generated by the ultrasound vibration of the probe. In some cases, the heat may burn a skin layer and a muscle layer of the body, which are in contact with the probe.

In order to prevent the burn by the heat generated from the probe, there is known a method which includes: inserting a heat-insulation protective member, which is made of, for example, plastic and has a through-hole into through the probe is to be inserted, into a hole drilled in the skin, and inserting the probe into the through-hole of the protective member to prevent the probe from coming into contact with surrounding tissues. However, since the method needs to use such an additional protective member in addition to the probe, it is necessary to drill a large hole in the skin at the time of operation. In addition, it may be difficult to control the probe while fixing the protective member.

In addition, an existing ultrasonic liposuction device needs to use an additional device for suctioning and removing crushed and emulsified adipose tissues. This may cause problems such as lengthening an operation time and increasing a fatigue level of an operator.

Accordingly, there is still a need to develop a device capable of efficiently performing the liposuction while minimizing the risk of burn due to the heat caused by the probe and ensuring patient safety.

SUMMARY

One object of the present disclosure is to solve the above-described problems in the prior art.

Another object of the present disclosure is to provide an ultrasonic device configured to prevent burn of surrounding tissues in a body at the time of liposuction.

Yet another object of the present disclosure is to provide an ultrasonic device configured to improve an efficiency of liposuction using ultrasound.

Representative configurations of the present disclosure to achieve the above objects are described below.

According to one aspect or the present disclosure, there is provided an ultrasonic device, comprising: a handpiece; an ultrasonic driving unit provided inside the handpiece; a probe including one end portion connected to the ultrasonic driving unit inside the handpiece and configured to extend outward of the handpiece from the one end portion; and a protection unit formed to extend along a longitudinal direction of the probe and to surround an outer circumferential surface of the probe, wherein a heat-insulation member may be provided in at least a portion of an inner circumferential surface of the protection unit.

According to one aspect of the present disclosure, the heat-insulation member may be provided adjacent to an extended end portion of the protection unit.

According to one aspect of the present disclosure, the protection unit may be provided to be spaced apart from the outer circumferential surface of the probe, and a flow path may be formed between the outer circumferential surface of the probe and the inner circumferential surface of the protection unit.

According to one aspect of the present disclosure, the protection unit may include at least one suction hole formed thereon and may be configured such that a crushed adipose tissue is introduced into a flow path formed between the probe and the protection unit via the at least one suction hole.

According to one aspect of the present disclosure, the protection unit may be formed to extend to a vibration node of the probe.

According to one aspect of the present disclosure, the protection unit may include a tapered portion formed on an extended end of the protection unit and may be configured to be in contact with the outer circumferential surface of the probe through the tapered portion.

According to one aspect of the present disclosure, a concave portion may be formed on at least a portion of the outer circumferential surface of the protection unit, and the heat-insulation member may be provided between one end portion of the protection unit and the concave portion.

According to one aspect of the present disclosure, the heat-insulation member may be formed of polypropylene.

According to one aspect of the present disclosure, the ultrasonic device may further include a fastening unit configured to removably connect the protection unit to the handpiece.

According to one aspect of the present disclosure, the fastening unit may be configured to be threadedly coupled to the protection unit.

According to one embodiment of the present disclosure, by providing a protection unit configured to surround a probe, it is possible to prevent burn due to heat generated from the probe without an additional protection member used in the prior art while minimizing the contact of the probe with surrounding tissues.

In addition, according to one embodiment of the present disclosure, it is possible to improve the efficiency of liposuction by simultaneously performing crush/emulsification and suction of an adipose tissue with a single device instead of with an additional suction device.

DETAILED DESCRIPTION

Figure 1:
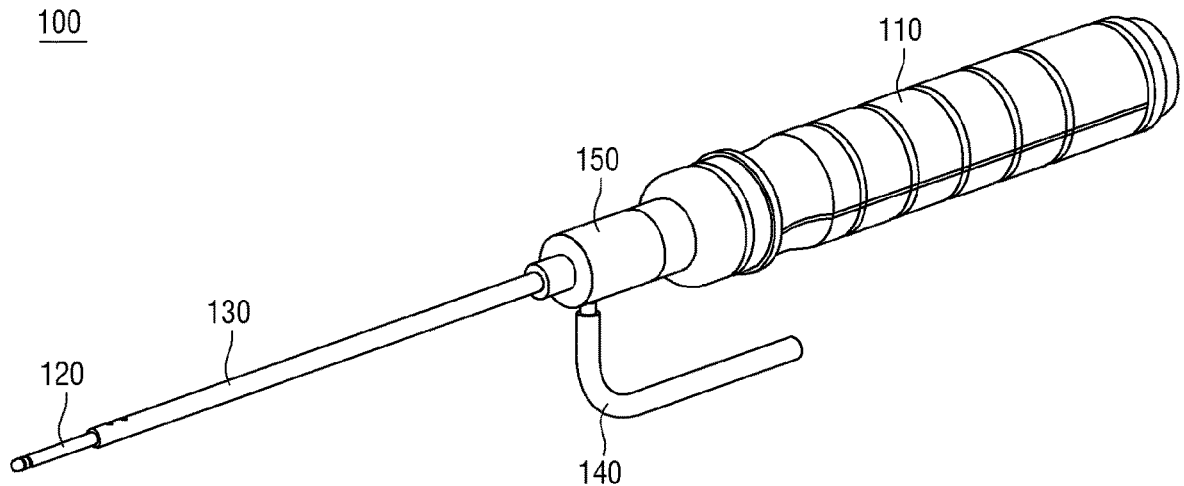
FIG. 1 is a perspective view of an ultrasonic device according to one embodiment of the present disclosure.

Hereinafter, exemplary embodiments of the present disclosure will be described in detail with reference to the accompanying drawings at such an extent that they may be readily practiced by those ordinary skilled in the art.

Throughout the present specification, when a constituent element is referred to as being "positioned" or "connected" to one side of another constituent element, the constituent element may be in direct contact with or directly connected to the one side of another constituent element, or may be positioned or connected to another constituent element by intervening yet another constituent element therebetween.

In order to clearly describe the present disclosure, detailed descriptions of parts irrelevant to the present disclosure will be omitted, and the same reference numerals will be given to the same constituent elements throughout the specification. Further, a size, thickness, position or the like of each constituent element illustrated in the drawings are arbitrarily illustrated for the sake of convenience in description, and hence the present disclosure is not necessarily limited to those illustrated. That is, it is to be understood that specific shapes, structures, and characteristics described herein may be modified from one embodiment to another embodiment without departing from the spirit and scope of the present disclosure. Positions or arrangements of individual constituent elements may also be modified without departing from the spirit and scope of the present disclosure.

Therefore, the detailed description described below is not to be taken in a limiting sense, and the scope of the present disclosure is to be taken as covering the scope claimed by the appended claims and their equivalents.

Figure 2:
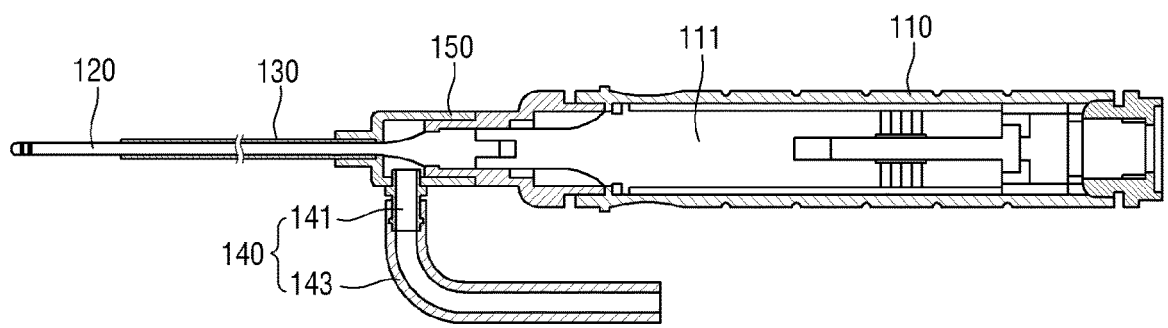
FIG. 2 is a cross-sectional view of the ultrasonic device according to one embodiment of the present disclosure.

FIG. 1 is a perspective view of an ultrasonic device according to one embodiment of the present disclosure, and FIG. 2 is a cross-sectional view of the ultrasonic device according to one embodiment of the present disclosure.

Referring to FIGS. 1 and 2, an ultrasonic device 100 according to one embodiment of the present disclosure, which is an apparatus that inserted into a body to crush and emulsify an adipose tissue by ultrasound, may include a handpiece 110, a probe 120, a protection unit 130, a suction unit 140, and a fastening unit 150.

The handpiece 110 of the ultrasonic device 100 according to one embodiment of the present disclosure corresponds to an unit held by a user to use the ultrasonic device 100. The handpiece 110 may have such a size and shape that allows the user to manipulate the ultrasonic device 100 by holding the ultrasonic device 100 with one hand.

According to one embodiment of the present disclosure, an ultrasonic driving unit 111 may be provided inside the handpiece 110. The ultrasonic driving unit 111 may be configured with an ultrasonic transducer that converts electrical energy into mechanical vibration energy, and a booster and a horn that reduce or amplifies an amplitude of the transducer. The ultrasonic driving unit 111 may be connected to an ultrasonic generator that converts an electric current into an ultrasonic current. In one embodiment, the ultrasonic transducer may be configured with a piezoelectric capable of generating ultrasonic vibration in a piezoelectric manner. However, the present disclosure is not limited thereto. An equipment that generates ultrasonic in other manners other than the piezoelectric manner may be used.

In one embodiment, the probe 120 to be described later may be connected to the ultrasonic driving unit 111. For example, a reception groove may be formed in one end portion of the ultrasonic driving unit 111, and one end of the probe 120 may be received in the reception groove to be fastened to the ultrasonic driving unit 111.

Further, the handpiece 110 may be formed of an insulating material, for example, a resin, which is capable of suppressing the transfer of heat generated from the ultrasonic driving unit 111. However, the present disclosure is not limited thereto. The handpiece 110 may be formed of other lightweight materials capable of providing an insulating effect without being uncomfortable to use for a long period of time.

The probe 120 of the ultrasonic device 100 according to one embodiment of the present disclosure may perform a function of crushing and emulsifying an adipose tissue. Specifically, the probe 120 may be inserted into the body, and crush and emulsify the adipose tissue while being placed near or in contact with the adipose tissue. Bubbles may be generated in a fat layer due to ultrasonic vibration of the probe 120. The adipose tissue may be separated and destroyed by cavitation caused by the generation of the bubbles, micromechanical destruction by rapid vibration, thermal effect by friction, and the like.

According to one embodiment of the present disclosure, the probe 120 may be configured such that one end portion thereof is connected to the ultrasonic driving unit 111 within the handpiece 110. The probe 120 may be configured to extend from the one end portion to the outside of the handpiece 110. In one embodiment, the probe 120 may include a proximal end portion coupled with the ultrasonic driving unit 111 provided within the handpiece 110, and a distal end portion formed to extend away from the ultrasonic driving unit 111.

In one embodiment, a coupling protrusion may be formed in the proximal end portion of the probe 120. The coupling protrusion may be inserted into and fastened to the reception groove formed in the ultrasonic driving unit 111 such that the probe 120 is connected to and coupled with the ultrasonic driving unit 111.

In one embodiment, the distal end portion of the probe 120 may be formed in a convex and gently-curved shape so as to minimize damage to surrounding tissues in contact with the probe 120 when being inserted into the body. In a position slightly spaced apart from the distal end portion of the probe 120, a groove may be formed along a circumferential direction of the probe 120. Such a groove may increase a contact surface area without increasing a diameter of the probe 120, thus increasing a rate at which the adipose tissue is crushed or emulsified.

According to one embodiment of the present disclosure, the probe 120 may be formed of titanium, titanium alloy, stainless steel, aluminum, or the like.

The heat generated by the ultrasonic vibration of the probe 120 as described above, may cause burns in a skin layer and a muscle layer inside the body. In order to solve this problem, the ultrasonic device 100 according to one embodiment of the present disclosure may include the protection unit 130. In one embodiment of the present disclosure, the protection unit 130 may prevent the skin layer and the muscle layer inside the body from coming into contact with an outer circumferential surface of the probe 120. This makes it possible to minimize the risk of skin burn and gangrene and ensure safety.

The protection unit 130 of the ultrasonic device 100 according to one embodiment of the present disclosure may perform a function of preventing the probe 120 from coming into contact with surrounding tissues such as skin. In one embodiment, the protection unit 130 may be formed to extend lengthwise along the longitudinal direction of the probe 120 and be formed in a form that surrounds the outer circumferential surface of the probe 120.

According to one embodiment of the present disclosure, the protection unit 130 may include a proximal end portion formed to extend in a direction oriented to the handpiece 110 and a distal end portion formed to extend in a direction away from the handpiece 110.

In one embodiment, the proximal end portion of the protection unit 130 may be configured to be coupled with the handpiece 110. Specifically, the protection unit 130 may be coupled with the handpiece 110 through the fastening unit 150 to be described below.

In one embodiment, the distal end portion of the protection unit 130 may be formed to extend to a vibration node of the probe 120. At least one vibration node may be formed in the probe 120 according to a length and ultrasonic frequency of the probe 120. The vibration node is positioned at a point where the intensity of ultrasound is substantially zero. An elastic stress and deformation rate of the probe 120 have maximum values at the position of the vibration node, and the greatest level of friction acts at the position of the vibration node. As a result, most heat is generated at the position of the vibration node. In one embodiment of the present disclosure, the protection unit 130 may be formed to extend to the vibration node, which is the point where most heat is generated in the probe 120. This makes it possible to more reliably suppress the heat from being transferred to the surround tissues such as skin at the time of surgical operation, and improve safety.

The protection unit 130 according to one embodiment of the present disclosure may have a heat-insulated structure and may be configured to discharge crushed and emulsified adipose tissues more easily. The configuration of the protection unit 130 will be described in detail below with reference to the drawings.

Figure 3:
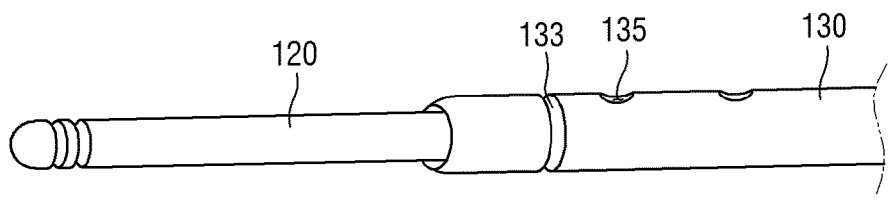
FIG. 3 is a view schematically illustrating a probe and one end portion of a protection unit according to one embodiment of the present disclosure.
Figure 4:
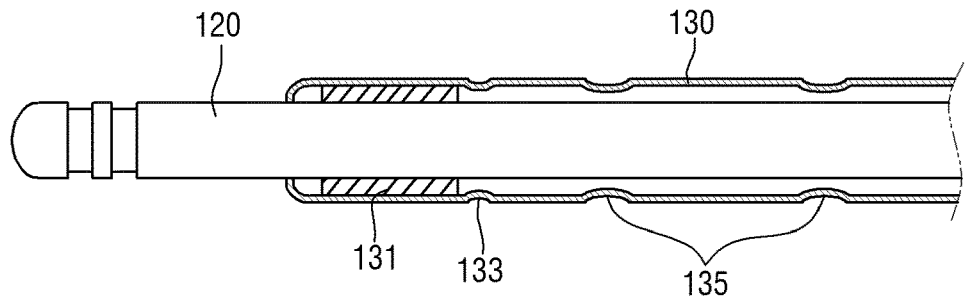
FIG. 4 is a view illustrating a partial cross section of FIG. 3.

FIG. 3 is a view schematically illustrating the probe and one end portion of the protection unit according to one embodiment of the present disclosure, and FIG. 4 is a view illustrating a partial cross section of FIG. 3.

Referring to FIGS. 3 and 4, a heat-insulation member 131 may be provided in at least a portion of the inner circumferential surface of the protection unit 130 according to one embodiment of the present disclosure. For example, the heat-insulation member 131 may be provided adjacent to an extended portion (i.e., the distal end portion) of the protection unit 130. In one embodiment, the heat-insulation member 131 may perform a function of preventing the probe 120 from coming into direct contact with the protection unit 130 to block the radiation of the heat generated in the probe 120 to the protection unit 130. According to one embodiment of the present disclosure, the heat-insulation member 131 may be formed of a plastic. For example, the heat-insulation member 131 may be formed of polypropylene (PP) with good biocompatibility, chemical resistance, high purity, low moisture absorption and good heat-insulation properties.

According to one embodiment of the present disclosure, a concave portion 133 may be formed in at least a portion of the outer circumferential surface of the protection unit 130 to separate a region where the heat-insulation member 131 is provided from the other region inside the protection unit 130, such that the heat-insulation member 131 is fixedly coupled to the inner circumferential surface of the protection unit 130. In one embodiment, the concave portion 133 may be formed along the circumference of the protection unit 130 at a position spaced apart from the distal end portion of the protection unit 130 by a size of the heat-insulation member 131. Thus, the heat-insulation member 131 may be provided between the distal end portion of the protection unit 130 and the concave portion 133.

According to one embodiment of the present disclosure, the protection unit 130 may be provided to be spaced apart from the outer circumferential surface of the probe 120. As a result, an annular flow path may be formed between the outer circumferential surface of the probe 120 and the inner circumferential surface of the protection unit 130. In one embodiment, a tapered portion may be formed in the extended portion (i.e., the distal end portion) of the protection unit 130 in a direction toward the outer circumferential surface of the probe 120 and may be brought into contact with the outer circumferential surface of the probe 120. Since the distal end portion of the protection unit 130 is in contact with the outer circumferential surface of the probe 120, crushed and emulsified adipose tissues is not allowed to be introduced between the distal end portion of the protection unit 130 and the probe 120. However, the present disclosure is not limited to such an embodiment. In order to maximize the effect of heat insulation using the protection unit 130, the distal end portion of the protection unit 130 may be formed to be spaced apart from the outer circumferential surface of the probe 120.

Structures and shapes of the protection unit and the heat-insulation member according to the present disclosure may be variously changed.

Figure 5:
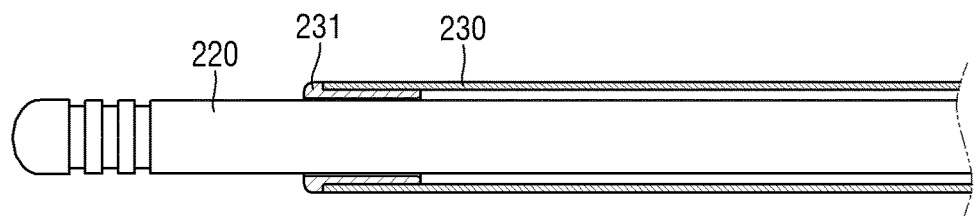
FIG. 5 is a view illustrating a partial cross-section of a probe and one end portion of a protection unit according to another embodiment of the present disclosure.

FIG. 5 is a view illustrating a partial cross-section of a probe and one end portion of a protection unit according to another embodiment of the present disclosure.

Referring to FIG. 5, a heat-insulation member 231 of a protection unit 230 according to another embodiment of the present disclosure may be formed integrally with an extended portion (i.e., a distal end portion) of the protection unit 230. The heat-insulation member 231 may be formed integrally with the distal end portion of the protection unit 230 by injection-molding. Specifically, at least a portion of the heat-insulation member 231 may be formed on an inner circumferential surface of the protection unit 230, and a portion (i.e., one end portion) of other portions of the heat-insulation member 231 may be formed to extend from the distal end portion of the protection unit 230 by a predetermined length. The one end portion of the heat-insulation member 231, which is the extended portion, may be formed thicker than at least a portion of the heat-insulation member 231 formed on the inner circumferential surface of the protection unit 230 by a magnitude corresponding to a thickness of the protection unit 230. The one end portion of the heat-insulation member 231 may have a shape that the thickness goes thinner toward the distal end, like an arrowhead. By such shape of the heat-insulation member 231, the protection unit 230 may be smoothly entered when the probe 220 is inserted into a body.

In this embodiment, the heat-insulation member 231 is formed integrally with the distal end portion of the protection unit 230 while extending from the distal end portion. Thus, the flow path formed between the outer circumferential surface of the probe 220 and the inner circumferential surface of the protection unit 230 is blocked, which makes it possible to prevent the crushed and emulsified adipose tissues from being introduced between the distal end portion of the protection unit 230 and the probe 120. Furthermore, since the distal end portion of the protection unit 230 is formed to be completely spaced apart from the outer circumferential surface of the probe 220, it is possible to maximize the heat-insulation effect by the protection unit 230.

Figure 6:
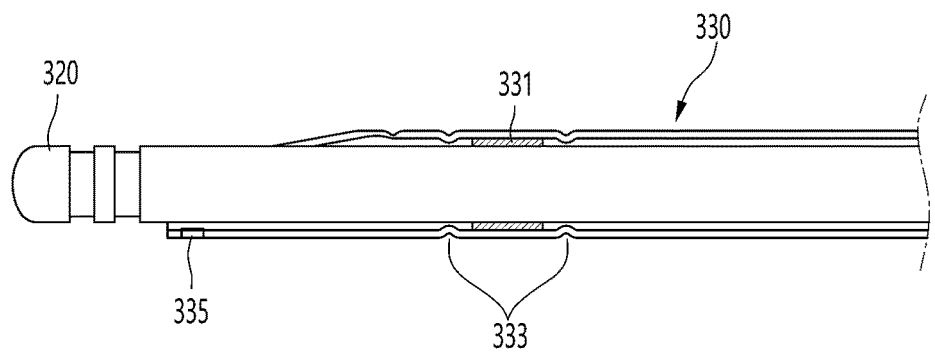
FIG. 6 is a view illustrating a partial cross-section of a probe and one end portion of a protection unit according to a further embodiment of the present disclosure.

FIG. 6 is a view illustrating a partial cross-section of a probe and one end portion of a protection unit according to a further embodiment of the present disclosure.

Referring to FIG. 6, the one end (i.e., the distal end) of the protection unit 330 according to the present embodiment may have an asymmetry shape. For example, the distal end of the protection unit 330 may have a shape of a cylinder which one side is obliquely cut. According to such shape of the protection unit 330, the protection unit 330 may be smoothly entered when the probe 320 is inserted into a body According to the present embodiment, a plurality of concave portions 333 may be formed on an outer peripheral surface of the protection unit 330, and a heat-insulation member 331 may be formed on an inner surface of the protection unit 330 and disposed between the plurality of concave portions 333.

Referring back to FIGS. 3 and 4, according to one embodiment of the present disclosure, at least one suction hole 135 may be formed on the protection unit 130. The at least one suction hole 135 formed on the protection unit 130 is used to suction adipose tissues crushed and emulsified by the ultrasonic vibration of the probe 120, and may be formed to be spaced apart from the point where the heat-insulation member 131 is coupled to the protection unit 130 on the side of in the proximal end portion of the protection unit 130. According to one embodiment of the present disclosure, crushed adipose tissues may be suctioned and introduced into the flow path formed between the outer circumferential surface of the probe 120 and the inner circumferential surface of the protection unit 130 via the suction hole 135 and move along the longitudinal direction of the probe 120 and the protection unit 130. Finally, the crushed and emulsified adipose tissues may be discharged through the suction unit 140 to be described later.

In the example embodiment illustrated herein, a total of four suction hole 135 may be formed with two suction holes along the circumferential direction of the protection unit 130 at a position spaced apart from the concave portion 133 and the remaining two suction holes along the circumferential direction of the protection unit 130 at a position spaced apart from the position where the two suction holes are formed toward the proximal end portion. However, the present disclosure is not limited thereto. The positions, number, and sizes of the suction holes may be variously changed according to the length and size of the protection unit. For example, as shown in FIG. 6, a suction hole 335 may be formed at a distal end side of the protection unit 330 comparing to the concave portion 333.

Referring back to FIG. 2, the suction unit 140 of the ultrasonic device 100 according to one embodiment of the present disclosure is a part for providing a suction force to the suction holes 135 formed in the protection unit 130, and may include a connection portion 141 and a suction tube 143.

According to one embodiment of the present disclosure, the connection portion 141 of the suction unit 140 may perform a function of connecting the suction unit 140 and the handpiece 110. In one embodiment, the suction unit 140 may be coupled to the handpiece 110 through the fastening unit 150 to be described below.

According to one embodiment of the present disclosure, the suction tube 143 of the suction unit 140 may be connected to an external suction pump (not shown) and may be configured to suction the crushed and emulsified adipose tissues through the suction unit 140 and the suction holes 135 of the protection unit 130 by virtue of a negative pressure generated by the suction pump.

The fastening unit 150 of the ultrasonic device 100 according to one embodiment of the present disclosure may perform a function of coupling the protection unit 130 and the suction unit 140 to the handpiece 110.

Figure 7:
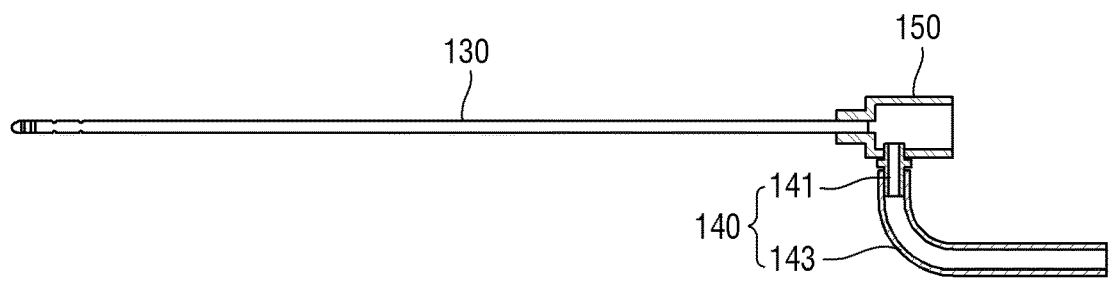
FIG. 7 is a view illustrating a state in which a protection unit and a suction unit are coupled to a fastening unit according to one embodiment of the present disclosure.

FIG. 7 is a view illustrating a state in which the protection unit and the suction unit are coupled to the fastening unit according to one embodiment of the present disclosure.

Referring to FIG. 7, the fastening unit 150 according to one embodiment of the present disclosure may be formed in a hollow cylindrical shape as a whole, and may have a configuration in which the protection unit 130 and the suction unit 140 may be coupled and connected to the fastening unit 150.

According to one embodiment of the present disclosure, one end portion of the fastening unit 150 may be configured to be removably connected to the handpiece 110. For example, the fastening unit 150 may be configured to be fitted into or screwed into the handpiece 110 so that a user may easily mount or remove the fastening unit 150. With this configuration, it is possible to improve not only user's convenience but also easily separate constituent elements such as the protection unit 130, the suction unit 140 from the handpiece 110, thus easily performing maintenance of such constituent elements.

According to one embodiment of the present disclosure, the other end portion of the fastening unit 150 may be configured to be coupled to the protection unit 130. In one embodiment, an inner circumferential surface of the other end portion of the fastening unit 150 and an outer circumferential surface of the proximal end portion of the protection unit 130 may have threads corresponding to each other, respectively, such that they are threadedly coupled to each other. In other words, the other end portion of the fastening unit 150 may be formed as a female thread and the proximal end portion of the protection unit 130 may be formed as a male thread such that they are threadedly coupled to each other. In one embodiment, the other end portion of the fastening unit 150 may be formed to surround the proximal end portion of the protection unit 130 at a predetermined length so as to stably fix the protection unit 130.

According to one embodiment of the present disclosure, the fastening unit 150 may be configured to be coupled to the suction unit 140 at one side thereof. In one embodiment, one lateral surface of the fastening unit 150 may have a hole formed to have a size corresponding to the connection portion 141 of the suction unit 140. By inserting the connection portion 141 into the hole or threadedly coupling the connection portion 141 to the hole, the suction unit 140 may be coupled to the fastening unit 150.

As described above, the ultrasonic device 100 according to the present disclosure includes the protection unit 130 configured to surround the probe 120 to minimize the direct contact of the probe 120 with surrounding tissues such as a skin. This makes it possible to prevent burn by the heat generated by the ultrasonic vibration without an additional protective member. Further, the suction holes 135 are formed in the protection unit 130, and the flow path through which the crushed and emulsified adipose tissues are introduced is formed between the protection unit 130 and the probe 120. This makes it possible to suction the crushed and emulsified adipose tissues through the suction unit 140. That is, the break-down and suction of the adipose tissue may be achieved by a single apparatus, which makes it possible to improve the efficiency of lipoplasty without using an additional suction device. Further, the protection unit 130 may be easily mounted and detached using the fastening unit 150, which makes it possible to easily perform maintenance and reuse the fastening unit 150 after cleaning.

Although the present disclosure has been described above in terms of specific items such as detailed constituent elements as well as the limited example embodiments, they are merely provided to help more general understanding of the present disclosure, and the present disclosure is not limited to the above example embodiments. Various modifications and changes could have been realized by those skilled in the art to which the present disclosure pertains from the above description.

Therefore, the spirit of the present disclosure need not to be limited to the above-described example embodiments, and in addition to the appended claims to be described below, and all ranges equivalent to or changed from these claims need to be said to belong to the scope and spirit of the present disclosure.

What is claimed is:

1. An ultrasonic device for an ultrasound-assisted lipoplasty, the ultrasonic device comprising:
   a handpiece;
   an ultrasonic driving unit provided inside the handpiece;
   a probe including one end portion connected to the ultrasonic driving unit inside the handpiece and configured to extend outward of the handpiece from the one end portion; and
   a protection unit formed to extend along a longitudinal direction of the probe and to surround an outer circumferential surface of the probe,
   wherein a heat-insulation member is provided in at least a portion of an inner circumferential surface of the protection unit,
   wherein the inner circumferential surface of the protection unit is provided to be space apart from the outer circumferential surface of the probe, and a flow path is formed between the outer circumferential surface of the probe and the inner circumferential surface of the protection unit,
   wherein the protection unit does not surround the distal end portion of the probe such that the distal end portion of the probe is exposed, and
   wherein at least one suction hole is formed on the protection unit and the heat-insulation member is located between an extended end portion of the protection unit and the at least one suction hole, thereby a crushed adipose tissue being introduced into the flow path via the at least one suction hole.

2. The ultrasonic device of claim 1, wherein the protection unit is formed to extend to a vibration node of the probe.

3. The ultrasonic device of claim 1, wherein the protection unit includes a tapered portion formed on the extended end of the protection unit and is configured to be in contact with the outer circumferential surface of the probe through the tapered portion.

4. The ultrasonic device of claim 1, wherein a concave portion is formed in at least a portion of the outer circumferential surface of the protection unit, and the heat-insulation member is provided between the extended end portion of the protection unit and the concave portion.

5. The ultrasonic device of claim 1, wherein the heat-insulation member is formed of polypropylene.

6. The ultrasonic device of claim 1, further comprising a fastening unit configured to removably connect the protection unit to the handpiece.

7. The ultrasonic device of claim 6, wherein the fastening unit is configured to be threadedly coupled to the protection unit.

\* \* \* \* \*